United States Patent [19]

Johnson et al.

[11] Patent Number: 5,263,489
[45] Date of Patent: Nov. 23, 1993

[54] RELATIVE ELECTROMYOGRAPHIC MUSCLE REFLEX ACTIVITY DURING MOTION

[75] Inventors: Michael T. V. Johnson; Alexander Kipnis, both of Minneapolis, Minn.

[73] Assignee: Empi, Inc., St. Paul, Minn.

[21] Appl. No.: 372,045

[22] Filed: Jun. 27, 1989

[51] Int. Cl.$^5$ ............................................. A61B 5/04
[52] U.S. Cl. ..................................... 128/733; 128/782
[58] Field of Search ............... 128/782, 733, 741, 724; 223/25; 364/413.27

[56] References Cited

U.S. PATENT DOCUMENTS

| | | | |
|---|---|---|---|
| 4,653,479 | 3/1987 | Maurer | 125/25 B |
| 4,688,581 | 8/1987 | Moss | 128/782 |
| 4,738,269 | 4/1988 | Nashark | 128/782 |
| 4,848,359 | 7/1989 | Bournonville | 128/741 |
| 4,885,687 | 12/1989 | Crey | 128/782 |
| 4,964,411 | 10/1990 | Johnson et al. | 128/733 |

OTHER PUBLICATIONS

"Myoelectric Responses of Flexors and Extensors of Human Wrist to Step Torque Perturbations" Robert Jaeger et al.—Journal of Neurophysiology Aug. 1982.

"Modulation of the Myotatic Reflex Gain in Man During Intentional Movements," J. Dufresne et al., *Brain Research*, 193 (1980) pp. 67-84.

"Stretch Reflex Modualtion During A Cyclic Elbow Movement," W. Mackay et al., *Electroencephalography and Clinical Neurophysiology*, 55 (1983) pp. 687-698.

*Primary Examiner*—Lee S. Cohen
*Assistant Examiner*—J. P. Lacyk
*Attorney, Agent, or Firm*—Kinney & Lange

[57] ABSTRACT

A method for treating electromyographic signals obtained from one or more muscles in the body which are subject to both volitional motion and externally forced motion to provide one or more indices which indicate the relative control signal energy provided to such a muscle or muscles during contractions and lengthenings thereof.

26 Claims, 10 Drawing Sheets

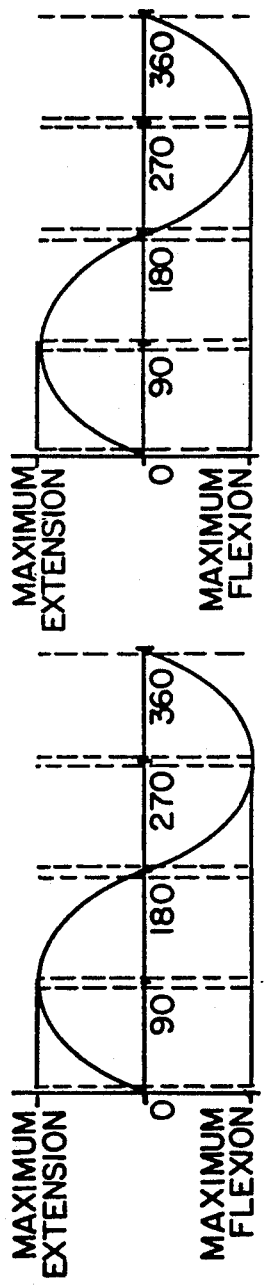
Fig.6A(i)
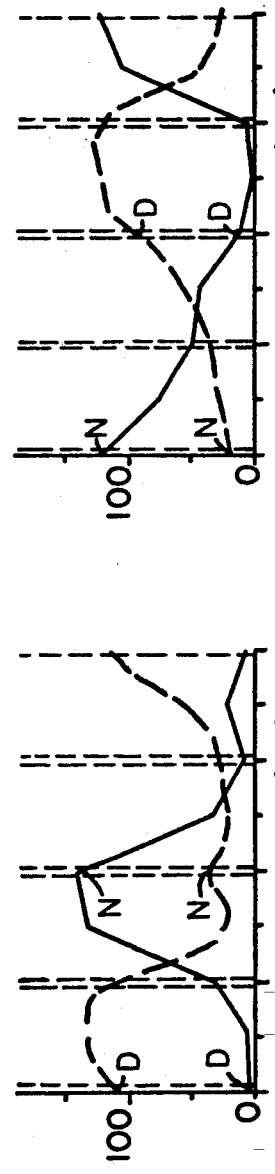
Fig.6A(ii)
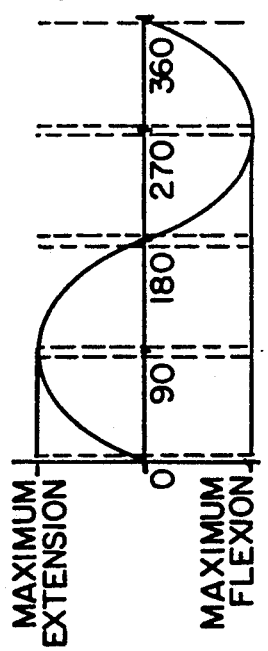
Fig.6A(iii)
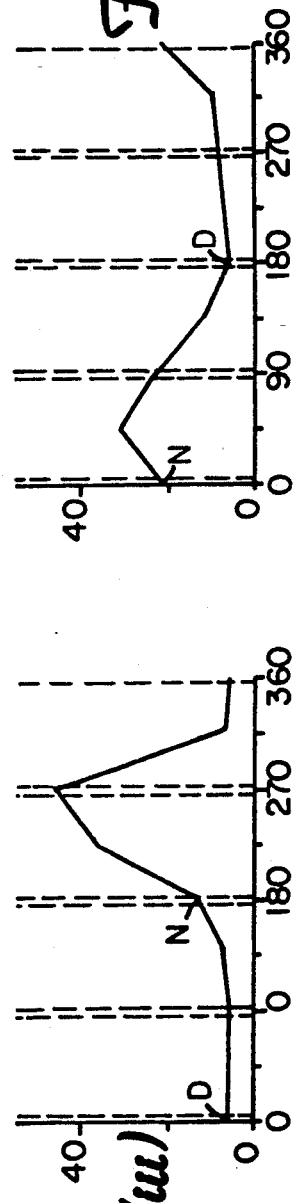
Fig.6B(i)
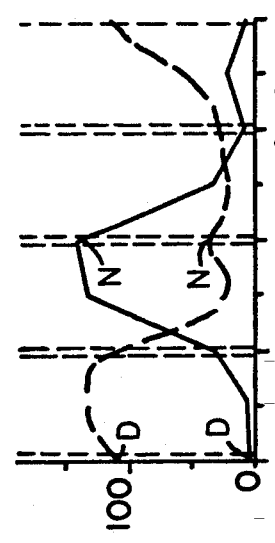
Fig.6B(ii)
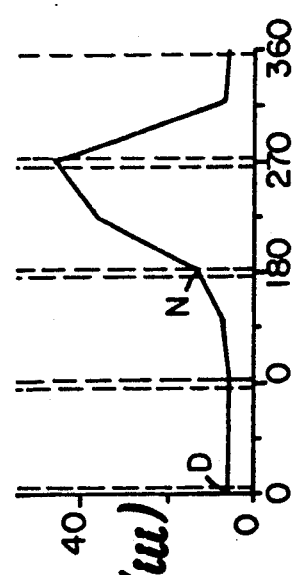
Fig.6B(iii)

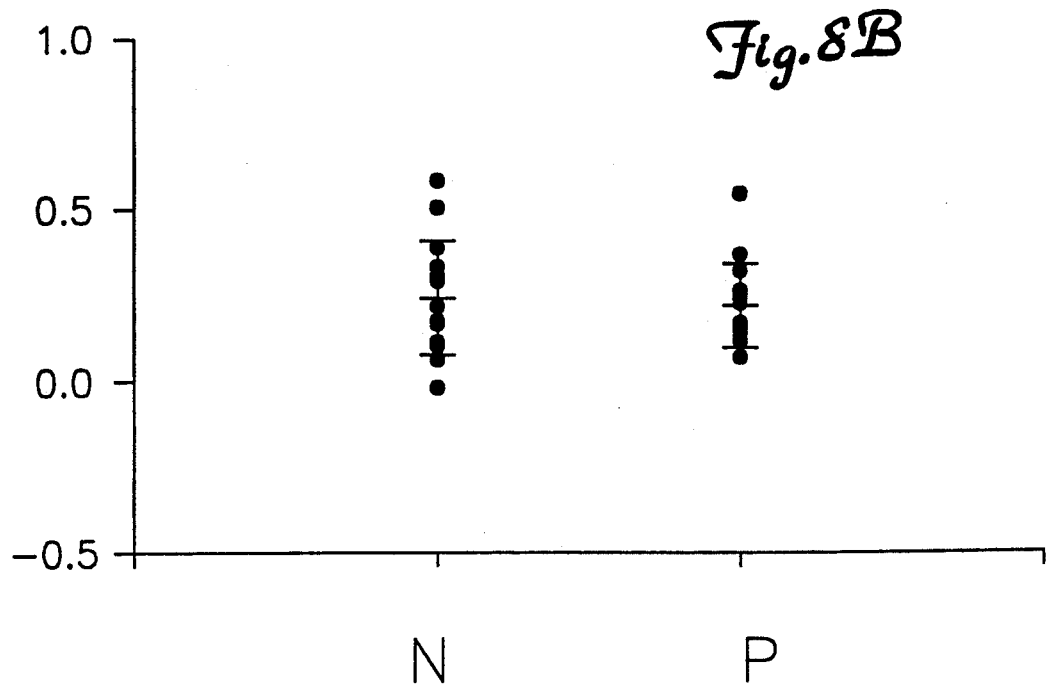
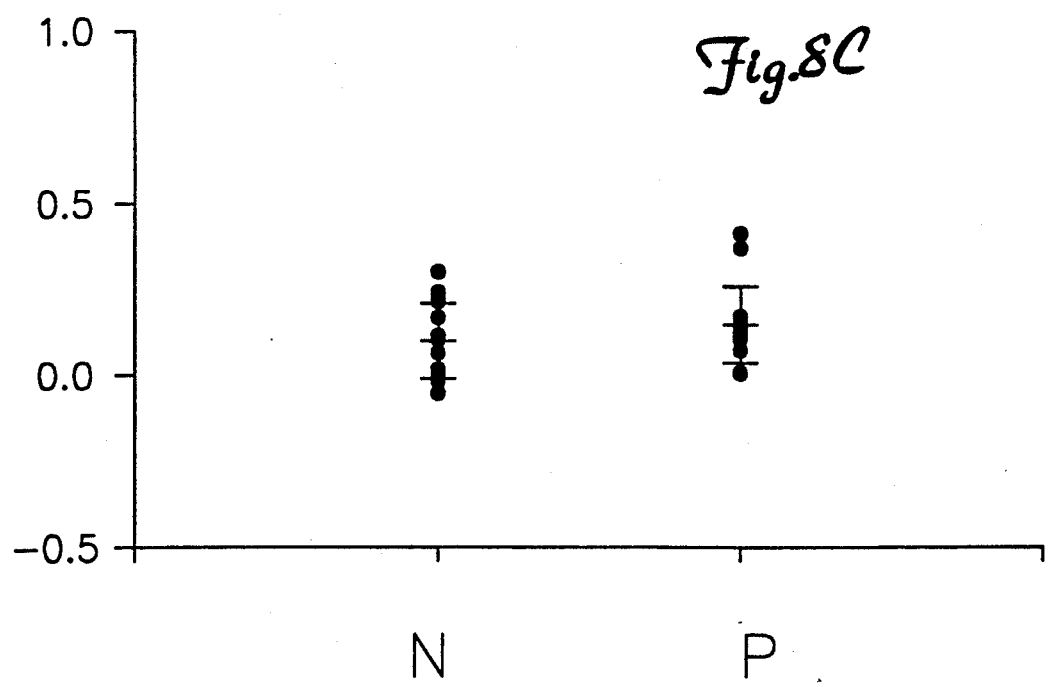

RELATIVE ELECTROMYOGRAPHIC MUSCLE REFLEX ACTIVITY DURING MOTION

BACKGROUND OF THE INVENTION

The present invention relates to determinations of relative muscular reflex activity during contractions and lengthenings of the body muscle involved as reflected in corresponding electromyographic signals and, more particularly, to such determinations made when the muscular contractions and extensions are involved with rotations of skeletal joints.

The control of the contracting and lengthening of muscles in the human body has long been known to have both a volitional aspect involving the central portions of the central nervous system and a reflex aspect involving peripheral portions of the central nervous system. In this latter aspect, the stretching of a typical muscle is sensed by a muscle spindle embedded therein and signals indicating such stretching are provided over afferent neurons to the system of spinal neurons. From there, return signals are provided over the alpha motor neurons, or efferent neurons, to the muscle body causing it to contract to counteract the initial stretching. This "local" feedback loop is the basis of reflex actions in the muscle involved.

In the former, or volitional, control aspect, a first mode of control has signals from the central portion of the central nervous system provided along the spinal nerve complex into the peripheral portion of the central nervous system. From there they are transmitted over alpha motor neurons to the muscle body to again cause it to contract.

However, the central portion of the central nervous system is also known to be able to affect or modulate the reflex actions of such a muscle. Thus, the level of signals in the reflex feedback loop described above appear subject to being increased (or decreased) under control of the central portion, i.e. in effect, the "gain" of that control loop can be changed by the central portion. Such a change in this stretch reflex feedback loop gain, i.e. modulation of the stretch reflex, is thought possibly to be due to signals provided from the central portion to the gamma motor neuron which extends to the muscle spindle or to influences exerted by the central portion on loop neurons (or interneurons) in the spinal nerve complex. Whatever the means, there is substantial evidence that movement of the muscle under volitional control is given effect not only through direct signals transmitted from the central portion of the central nervous system through the spinal nerves and over the alpha motoneuron to the muscle, but also through the central portion transmitting signals having the effect of modulating the stretch reflex.

As is well known, muscles in moving structural portions of which they are comprised, and other bodily structures to which such muscles are connected, are capable of being forced to contract in length but, in the other direction, are merely permitted to lengthen under some externally applied tensile force. That is, lengthening of a muscle cannot be forced solely by signals transmitted over motor neurons to that muscle. Thus, skeletal joints in the human body are operated by pairings of muscles to permit them to be rotated in opposite directions.

A member of such a muscle pair for such a skeletal joint is provided more or less on opposite sides of that joint and each is capable of rotating the actuator portion of that joint, with respect to the base portion of that joint, under a forced contraction thereof toward itself. Hence, each member of that muscle pair can cause a rotation of the actuator portion of that joint in a direction opposite to that which the other member can cause a rotation to occur under a forced contraction of that member. Thus, normal control of the rotation of an actuator portion of a skeletal joint with respect to its base portion requires that the contracting muscle on the side of the joint toward which the actuator portion is drawn during its contraction, or the agonist muscle, be accompanied by the absence of any significant contracting activity in the muscle on the opposite side of the joint, or the antagonist muscle.

Thus, a volitional movement of the agonist muscle to rotate the actuator portion of the skeletal joint toward it requires signals from the central portion of the central nervous system to be directly sent to the agonist muscle without a similar direct signal sent to the antagonist muscle. In addition, the stretch reflex modulation directed by the central portion is to be concomitantly increased in the agonist muscle but should not be increased in the antagonist muscle, or should be inhibited in this antagonist muscle. That is, co-contraction of the agonist and antagonist muscles should be avoided for proper rotation in most circumstances of the actuator portion of the joint. To this end, there is evidence of reciprocal inhibition being associated with the stretch reflex in the human body so that stretch reflex modulation associated with the agonist muscle is accompanied by an inhibition of that reflex in the antagonist muscle.

There are, unfortunately, many situations in which proper control of rotations of a skeletal joint in the human body is lacking or degraded. Among the movement disorders associated with the skeletal joints are spasticity, dystonia, cerebellar hypotonia, and bradykinesia, with this latter term referring to the abnormalities of volitional movement evident in some sufferers of Parkinson's disease. Bradykinesia refers to a variety of volitional movement difficulties including slow onset of movement with respect to a given stimulus, reduced amplitude of movement in reaching a goal position after a stimulus, reduced peak velocity of such movements, and rapid fatigue occurring with repetitive movements. Bradykinesia is considered to be independent of the other major groupings of symptoms associated with Parkinson's disease, muscular rigidity and resting tremors. Concerning these symptom types, bradykinesia is a major factor responsible for the disability experienced by those suffering from Parkinson's disease.

Just what defects in the central nervous system that are caused by Parkinson's disease also lead to bradykinesia has not been well understood. Studies of rapid joint movements, or ballistic movements, have demonstrated that abnormalities occur both in associated electromyographic signals and in the movements themselves in those suffering from Parkinson's disease. Studies based on having sufferers of this disease operating one of their skeletal joints to track a target based on visual guidance have also demonstrated defects in such sufferers' performance at those kinds of tasks. Much of the evidence uncovered in such studies have been used to implicate defects in the central portion of the central nervous system as the cause of bradykinesia.

However, studies of sufferers of Parkinsonism, based on supplying a stimulus to initiate volitional movement, have shown that changes with respect to those not so suffering in reaction time to that stimulus, or the time duration to first movement thereafter, are independent of the increases in total movement time following such a stimulus for the actuator portion of the joint to reach a position goal. This suggests that even though the volitional signals have been clearly provided from the central portion of the central nervous system to the muscles controlling the joint, there are also difficulties in the peripheral portion of the central system retarding the carrying out of the desired motion by sufferers of Parkinson's disease.

There has recently been found evidence indicating that a defect or defects in the stretch reflex during the execution of a skeletal joint movement may be responsible for at least some aspects of bradykinesia. There is evidence suggesting that such a volitional movement, which should be based on coordinated direct signals from the central portion of the central nervous system to the agonist muscle involved and indirect signals from that central portion to modulate its stretch reflex, are not properly coordinated in achieving a desired motion. Such a lack of coordination provides the possibility of the agonist and antagonist muscles associated with the skeletal joint having overlapping contracting activity so that one is braking the activity of the other to an extent. A determination of the extent of such braking, for purposes of determining the extent of bradykinesia in Parkinson's disease in the sufferer, would be desirable. In addition, such a determination could be used to evaluate therapeutic strategies and to set levels of pharmacologic therapy.

SUMMARY OF THE INVENTION

The present invention provides a method for treating electromyographic signals obtained from one or more muscles in the body which are subject to both volitional motion and externally forced motion to provide one or more indices which indicate the relative control signal energy provided to such a muscle or muscles during contractions and lengthenings thereof. Electromyographic signal portions are acquired from a muscle, or a pair of muscles such as an agonist-antagonist pair, which are taken both when the muscle or muscles are contracting and when lengthening, and further when an external force is applied to the muscle or muscles and when its not. Selected ones of these electromyographic signal portions, or representations thereof, are used to form indices indicative of the relative electromyographic signal strengths for both reflex initiated motion components and volition initiated motion components during muscle contraction and muscle lengthening, and further, indicative of joint signal strengths of paired muscles. Such electromyographic signal portions in such conditions are conveniently acquired by having a human direct the actuator side of a joint in that human's body to follow a specified reciprocating position target while subjecting that side of the joint to selected external forces applied for a selected time on selected occasions during such target tracking.

BRIEF DESCRIPTION OF THE DRAWINGS

FIGS. 8A, 8B and 8C show comparative plots of values of indices found for selected subjects obtained from the use of the apparatus of FIG. 1 with such subjects.

DETAILED DESCRIPTION OF THE PREFERRED EMBODIMENTS

Figure 1:
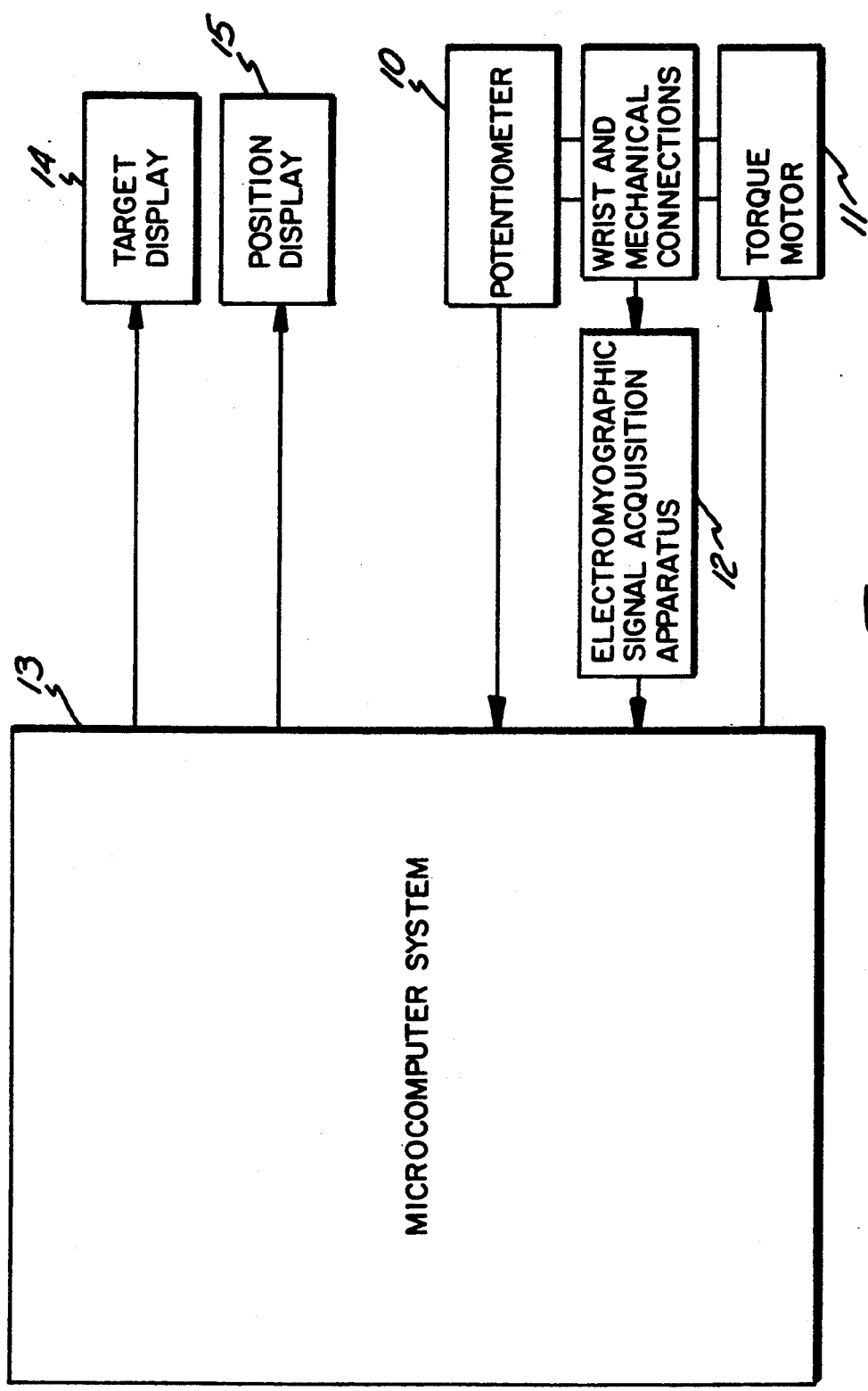
FIG. 1 shows a block diagram of apparatus used in practicing the present invention.

FIG. 1 shows a block diagram of a testing arrangement used in practicing the present invention. The subject of a test in this arrangement has his or her dominant side forearm horizontally immobilized by a bracing arrangement located close to the wrist but leaving the location of the muscle bulk of the muscles operating that wrist exposed so that electrodes for acquiring electromyographic signals can be placed thereon. The forearm of the subject is immobilized in such a manner that the base of the thumb of the hand of that forearm would be in an approximately superior position on a vertical axis so as not to impede the sliding of tendons or the contracting and lengthening of the muscles operating the wrist.

The hand of such a subject is secured to a low mass handle in a manner so as to keep that hand in a position of a neutral grasp for operating purposes. That handle is secured both to a potentiometer, 10, and to a torque motor, 11, as indicated in FIG. 1. The handle connected to potentiometer 10 and torque motor 11 is permitted to easily and conveniently rotate about a vertically oriented axis, and to receive torques about such an axis, with this vertical axis being more or less collinear to the axis of rotation of the wrist in the position thereof established as indicated above.

Electromyographic signal acquisition apparatus, 12, of a well known kind, is used to acquire the necessary electromyographic signals from the muscles operating the wrist. The electromyographic signals are sensed using circular 4.0 mm diameter silver-silver chloride transcutaneous or surface electrodes placed over the major bulk of two wrist operating muscles on either side of the forearm, the flexor carpi ulnaris and the extensor carpi radialis. Three such electrodes are provided on each of these muscles, two sensing electrodes that are 6.0 to 10.0 cm apart longitudinally over the maximal palpable bulk of the muscle with a reference electrode placed between each of such sensing electrode pairs on that muscle.

A microcomputer system, 13, is used to display a moving target formed by a source of light that is small with respect to the path dimensions, and which follows a reciprocal positioning scheme in that the target oscillates in position in a sinusoidal manner. The subject being tested is to attempt to track this target through moving the handle described above to which his or her hand is attached to follow the positional changes of that target.

Microcomputer system 13 also controls torque motor 11 by selectively supplying current pulses thereto each of which causes a corresponding impulsive torque of a selected duration and amplitude to be delivered from torque motor 11 to the test subject's hand through the same handle indicated above to which the hand of the subject of the testing is connected during his or her tracking efforts. Such torque pulses, or torques, each force the wrist joint of that subject for the hand connected to the handle to rotate as that hand is forced toward either a flexion position with the palm of the hand coming toward the forearm or to an extension position with the back of the hand coming toward the forearm.

A target display, 14, is shown to the subject during testing under control of microcomputer 13 as a horizontal bar display comprising 101 light emitting diode elements set out in a linear array of approximately 10.0 cm length. At typical viewing distances for the subject and with typical target rates of motion, the individual light emitting diode elements appear subjectively fused into a line shape. An impression of continuous target motion results when successive elements are driven in sequence following selected points in a sinusoidal position function at the frequencies of oscillation, or position reciprocation, used in the testing.

Microcomputer system 13 at the same time also acquires data on actual wrist position from precision potentiometer 10 for display so that the subject can view his or her success in tracking the target. A display, 15, similar to the one used to display the target is used to show the subject the actual position achieved by his or her hand rotating about his or her wrist joint to move the handle to follow the target. The subject under test attempts to match the two displays by moving his or her hand about the wrist joint in such a manner as to cause the actual position indicated on display 15 to match that of the target shown on display 14. In the sinusoid wave form generated by microcomputer 13 to set the position of the target in display 14, a zero amplitude value occurs at approximately the neutral position of the wrist between extension and flexion, and the value of the amplitude at 90° and 270° on that sinusoid represents maximum extension and maximum flexion, respectively. Microcomputer 13 selectively generates current pulses which, under certain conditions, are delivered to torque motor 11 to cause it, as described above, to provide corresponding impulsive torques at its output to the handle to which the subject's hand is attached to stretch the muscles being measured to elicit a stretch reflex therefrom. Microcomputer 13 accomplishes this through use of a digital-to-analog converter and suitable amplification to provide a sufficient current pulse. The peak amplitude of the torque step is in the range of 0.5 to 0.75 Newton-meters with a duration of approximately 250.0 ms. The direction of the torque delivered, whether forcing the hand in a direction to cause greater flexion or to cause greater extension when delivered at selected times during tracking, i.e. at selected phase points of the tracking sinusoid, is determined on a random basis by microcomputer 13.

In practice, such impulsive torques are provided to the hand of the subject being tested, if at all, at only the 0°/360° point (assuming the remaining parts of the sinusoid to be repetitions of its initial cycle rather considering it to be multiple cycles of a constantly increasing angle) the 90° points, the 180° points and the 270° points of the tracking sinusoid, and then only if the subject's hand position matches the computer generated target within a specified error at those potential impulsive torque deliverance phase points of the target position sinusoid. Typical error limits would be that the hand angular position with respect to the forearm is within 3° of the target when within 100 ms from the selected torque deliverance phase points in the target position sinusoid. Failure of the subject to track within these error limits causes microcomputer 13 to avoid causing torque motor 11 to deliver an impulsive torque and eliminates any data collected during that position cycle to insure similar sinusoidal volitional tracking behavior at the time of each such delivered torque impulse.

In any event, at each of these potential impulsive torque deliverance phase points, microcomputer 13 not only randomly selects the direction of any impulsive torque applied to the subject's hand, but also on a random basis determines whether any torque pulse will be delivered at all at any one of these phase points at each occurrence thereof during the target position cycles. Such non-delivery of a torque impulse at such a phase point means that is no stretching of the measured wrist operating muscles so that no stretch reflex electromyographic signal activity is present, and so only volitional directive electromyographic signal activity is in that instance available for measure.

The angular position of the subject's wrist, and the electromyographic signals obtained by apparatus 12 from the extensor and flexor muscles, are acquired through an analog-to-digital converter sampling the signals at a rate of 2,000 samples per second which samples are then provided as digital words of 12 bits each. The electromyographic signals obtained from the electrodes are amplified in apparatus 12 from 5,000 to 20,000 times before conversion as is determined to be needed for a particular subject and the equipment of FIG. 1. A bandpass filter in that amplifier filters the analog signals obtained from the electrodes at the wrist before providing them to the analog-to-digital converter therein, with the bandpass filter characteristic having cutoff frequencies at 10 and 300 Hz.

Microcomputer system 13 in addition provides for recording of the data obtained from the electromyographic signal acquisition apparatus 12. Further, data with respect to handle and so angular position of tested wrist with respect to its forearm, is similarly recorded thereby from potentiometer 10. The signal processing of this data in a manner to be described below can also be accomplished by microcomputer 13 and the results thereof stored in a similar manner.

A subject to be tested is instructed to track the position of the target by moving the handle while remaining relaxed and attempting to avoid any reaction to the torque pulses except to continue to attempt to track the target. The subject is to be discouraged from active grasping of the handle to avoid causing activation of the long finger flexor-extensor muscles which would generate electromyographic signals that could mix with those being measured in connection with the wrist flexor and extensor muscles. A practice period is provided ahead of time to the subject to have that subject achieve a desired competence level before beginning any testing. The subject then typically performs two series of tests of ten repetitions each. The results of these two series are averaged by microcomputer 13 based on the data supplied thereto from electromyographic signal acquisition apparatus 12.

In addition to the averaging of the two test series, the data that is desired to be obtained are the electromyographic signal samples which occur after the successful tracking of the target position past each of the potential impulsive torque deliverance phase positions along the target position sinusoid in each cycle, these again being the 0°/360°, 90°, 180° and 270° phase points at which an impulse of torque may, on a random basis, be delivered to the handle and so to the hand of the subject. This electromyographic signal data from the electrodes over the selected wrist operating muscles indicated above, having any amplifier offsets and the like removed, is collected for 120 ms after the imposition of an impulsive torque, or after the passing of such a phase point without such an imposition. Such data collected is digitally rectified so that it is of a single polarity.

The resulting electromyographic signal sample points for each such collection are grouped into 12 groups, each representing the points collected in a 10 ms interval of the entire 120 ms data collection duration. The average signal value is found for the signal samples in each of these groups. A further averaging of these averages is taken for each such collection of data over the number of repetitions during testing of identical collection conditions. That is, the 12 group time averaged values resulting from a collection of data at each potential impulsive torque deliverance phase point along the target position sinusoid are averaged with the other collections that occur at that phase point, averaging those occurring there with an imposition of an accompanying impulsive torque among themselves and averaging those without such an accompaniment among themselves.

Thus, electromyographic signal averages representative of volitional directives to the muscles involved are acquired at each potential impulsive torque deliverance point along the target position sinusoid for the averages of those electromyographic signal portions which occurred in the absence of any impulsive torque being delivered at those points. Mixed reflex and volitional electromyographic signal averages are acquired at each potential impulsive torque deliverance point along the target position sinusoid by averaging those electromyographic portions which occurred when accompanied by the occurrence of an impulsive torque. These mixed averages are converted to essentially stretch reflex only electromyographic signal averages by subtracting from the former the averages representing the volitional electromyographic averages previously described. Alternatively, division could be used rather than subtraction.

As a result, a volition matrix of 12 rows and four columns is obtained from the volitional based electromyographic signal averages and a similar reflex matrix is obtained from the stretch reflex based electromyographic signal averages for each subject tested. Each of the 12 rows represents the average of the rectified electromyographic signals for one of the twelve 10.0 ms time intervals in the 120 ms duration data collections following successful tracking through each potential impulsive torque deliverance point. Each of the columns represents one of the four potential impulse torque deliverance phase points along the target position sinusoid cycle at which the data collections were taken.

These two matrices, the volition electromyographic data matrix and the reflex electromyographic data matrix, contain the information on the control directives provided to the muscles involved in operating this wrist at the selected points during the prescribed volitional movement, and the information on the stretch reflex response of those muscles at selected points in such movement. They thus provide the basis for making a determination of whether the modulation of the stretch reflex for these muscles is properly coordinated with the volitional directives thereto during contractions and lengthenings thereof.

One way of presenting this data to an observer is to provide a graphical representation to permit at least qualitative analysis thereof, and this may be done by expanding these matrices to 36 row by 12 column matrices using inverse distance weighted linear interpolation. The elements thus generated are used to form closed contours (some closed by plot borders) on a plane having cartesian axes with data collection time duration (following successful target tracking through potential impulsive torque deliverance points) on one axis in milliseconds, and the target position sinusoid cycle phase in degrees on the other axis. Each contour in a plot is drawn by interpolation between values provided from this expanded matrix through points having a common selected value of electromyographic signal strength with each contour in a plot having a different selected common value as its basis. A first pair of such plots corresponding to a tested individual are shown in FIGS. 2A and 2B.

Figure 2A:
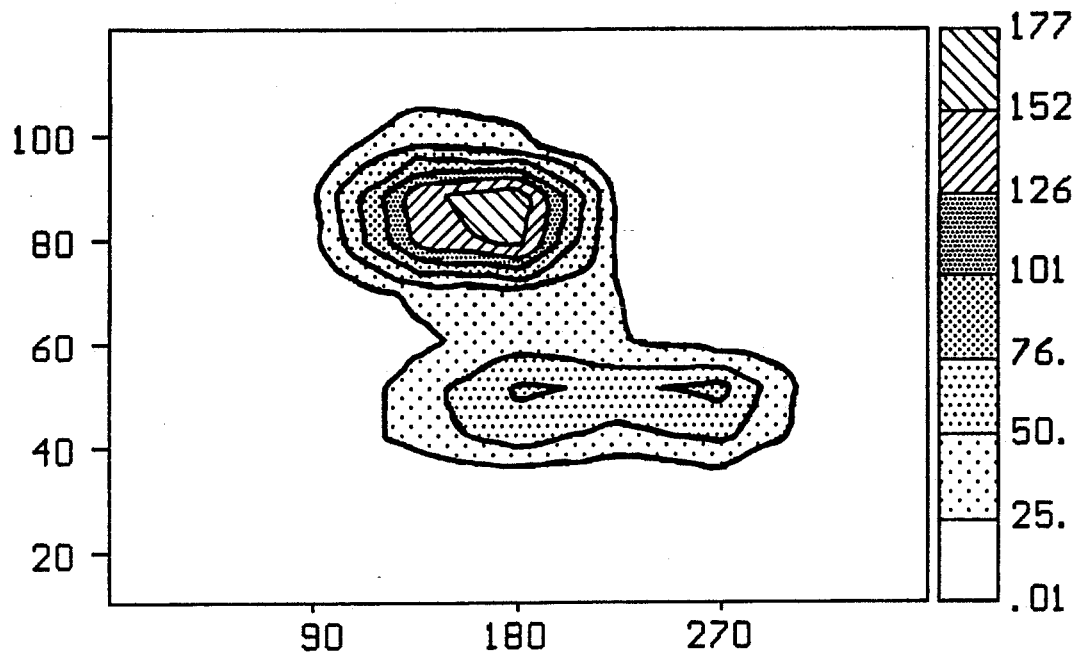
FIGS. 2A and 2B show data of three dimensions obtained from use of the apparatus of FIG. 1 with a selected subject in a two dimensional plot.
Figure 2B:
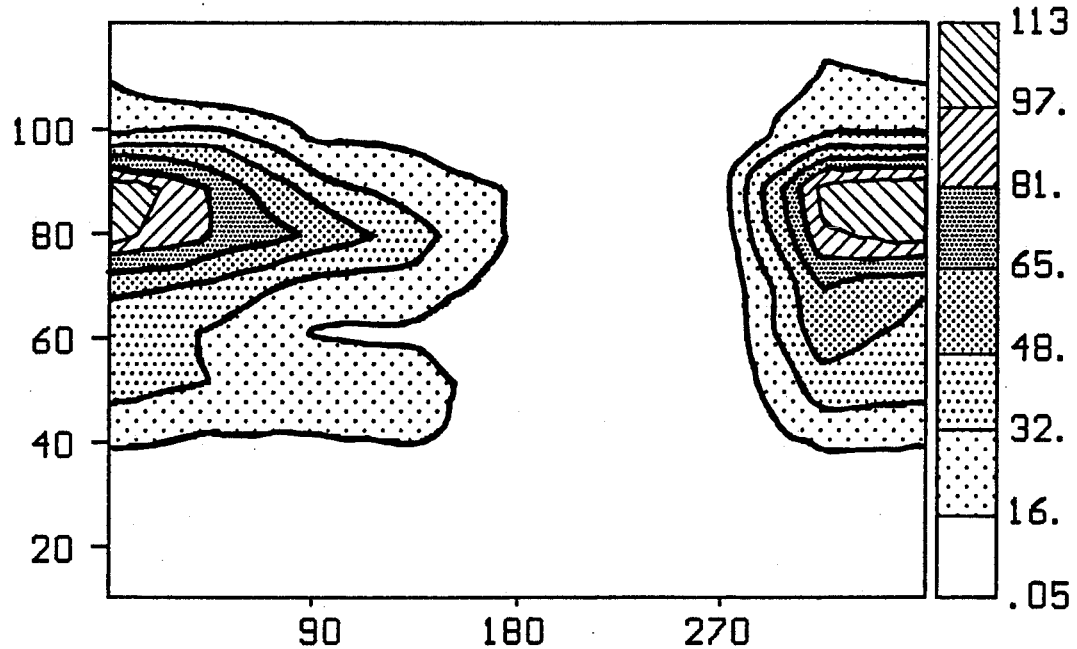

FIGS. 2A and 2B show plots resulting from the two reflex matrices obtained by testing two wrist operating muscles as described above for a normal subject not suffering from Parkinson's disease. FIG. 2A has time in milliseconds plotted along the ordinate axis with zero representing the time at which an impulsive torque was applied through the handle to the hand of the subject at one of the potential impulsive torque deliverance phase points in the target position sinusoidal cycle. The phase of such cycles is shown in degrees along the abscissa axis. A vertical bar shading chart is shown to the right in which the range of values of the electromyographic signal averages for each shading type is given.

FIG. 2A shows the measured electromyographic stretch reflex averages of the above-noted flexor wrist operating muscle involved from which data was obtained during testing of the subject's wrist. Repeating, the phase points of 0°/360° and 180° represent the neutral point of the hand between flexion and extension with respect to the wrist. However, since the 90° phase point represents maximum extension and the 270° phase point represents maximum flexion of the wrist joint, the phase point 0°/360° represents the wrist coming to the neutral position after the completion of a maximum flexion so that hand velocity and wrist angular rotation rate are at a maximum in approaching the next full extension. On the other hand, 180° represents the hand reaching a neutral position with respect to the wrist after the last extension and represents the point at which that hand velocity and rotation rate of the wrist are reaching a maximum in the next approach of the hand to full flexion.

As can be seen in FIG. 2A, the signal strength in the electromyographic signals is heavily concentrated about the 180° phase point which is where the flexor muscle is most rapidly contracting so as to have the hand velocity and the wrist rotation rate to reach a maximum in causing the hand to reach the next full flexion position. Thus, the electromyographic signals associated with the stretch reflex are clearly happening at a time when they will aid the volitional electromyographic signals which are directing the hand to go to a full flexion position.

FIG. 2B represents a plot of the same nature as that of FIG. 2A, but for the corresponding extensor muscle of the same subject. As can be seen here, electromyographic signal strength is strongly concentrated about the 0°/360° phase point where the contracting of that muscle has the hand velocity and the angular rotation rate of the wrist reaching a maximum in causing the hand to next approach the full extension position. Again, these signals are clearly occurring in the proper phase to be able to have the stretch reflex aid the volitional directives to move the hand to a full flexion position.

Figure 3A:
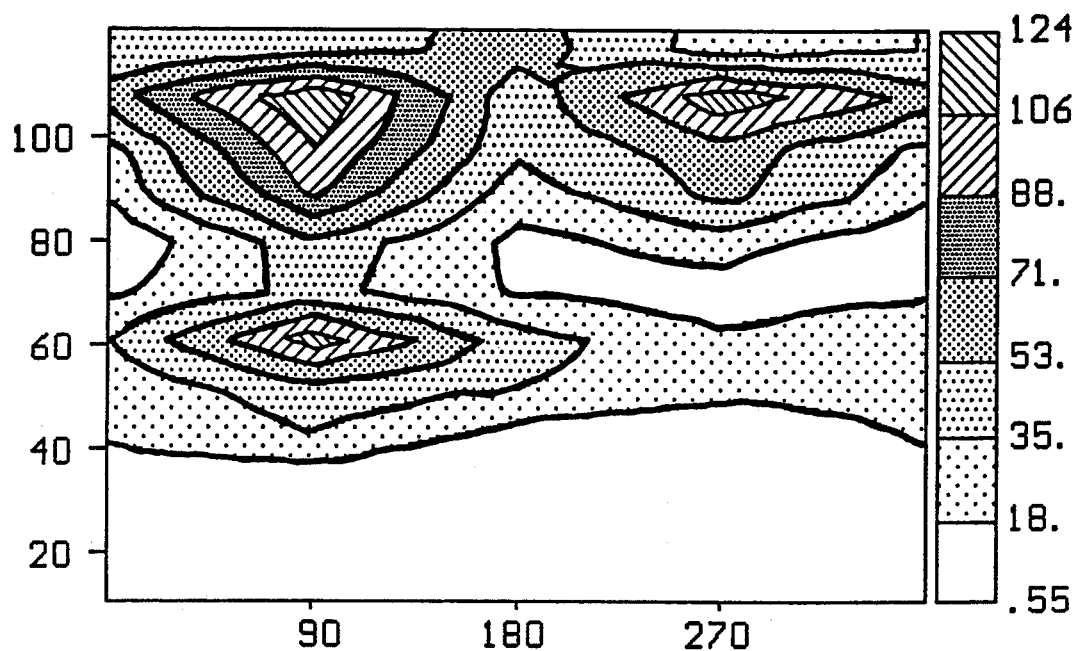
FIGS. 3A and 3B show data of three dimensions obtained from use of the apparatus of FIG. 1 with a selected subject in a two dimensional plot.
Figure 3B:
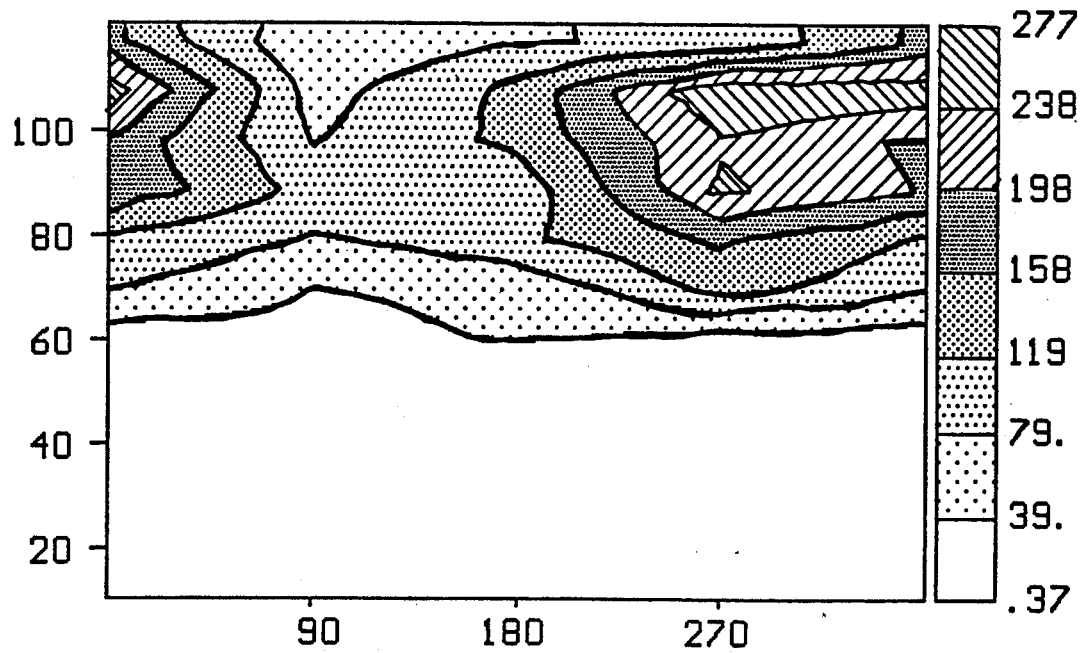

FIGS. 3A and 3B, on the other hand, show the results for a subject who suffers from Parkinson's disease. FIG. 3A shows that for the flexor muscle the electromyographic signal strength, rather than being concentrated at 180°, is instead concentrated at 90° and somewhat at 270°. Thus, the stretch reflex is acting at points in time primarily when the hand has taken either the maximum extension position or the maximum flexion position rather than when the flexor muscle is to be contracting at its maximum to cause the hand to be driven toward its next maximum flexion position.

As a result, there is significant electromyographic signal strength due to the stretch reflex occurring in the wrong time with respect to the volitional directives to be of aid in bringing the hand to this next flexion position, and some of this stretch reflex activity is clearly occurring where the extensor muscle is to have its strongest contractions and so is acting to brake the motion toward this next maximum extension position rather than aiding the reaching of it. FIG. 3B, on the other hand, appears much more like that of a normal person not suffering from Parkinson's disease indicating that the extensor muscle stretch reflex is still properly coordinated with the volitional directives in moving the hand toward its next maximum extension position. Thus, the stretch reflex modulation is defective only with respect to the flexor muscle.

Figure 4A:
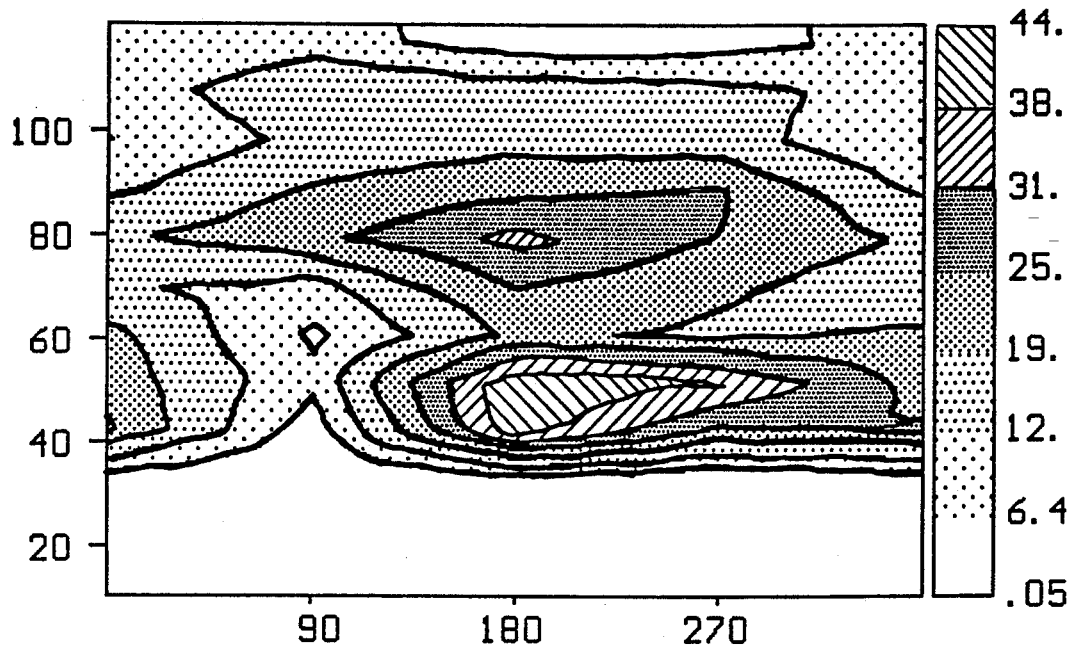
FIGS. 4A and 4B show data of three dimensions obtained from use of the apparatus of FIG. 1 with a selected subject in a two dimensional plot.
Figure 4B:
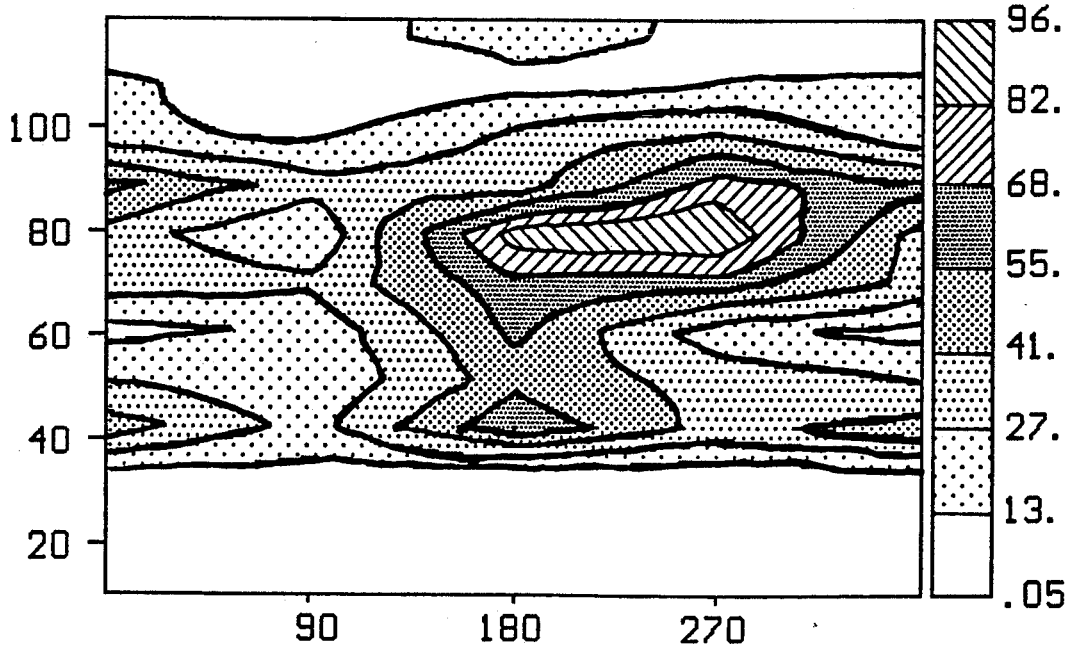

FIG. 4A and 4B represent the testing of another subject with approximately the opposite results with respect to the previous subject of FIGS. 3A and 3B. FIG. 4A shows that the electromyographic signal strength is concentrated at the 180° for the flexor muscle involved, just as it should be for having the stretch reflex capabilities of that muscle aid the volitional directives in causing the hand to reach the next full flexion position.

On the other hand, the extensor muscle electromyographic signal strength is also concentrated near 180° with the result that the stretch reflex of this muscle is acting to brake the motion of the hand by acting against the flexor muscle in having the hand attempt to reach full flexion while failing to aid the volitional directives to the extensor muscle to reach full extension. Clearly here, there is a defect in the stretch reflex of the extensor muscle.

Figure 5A:
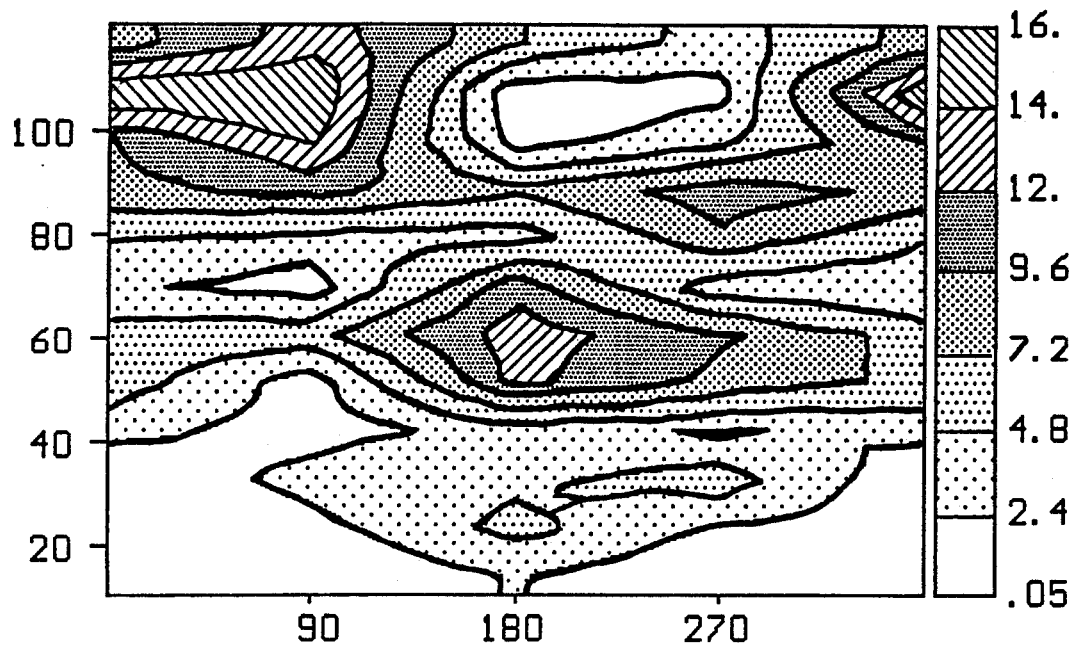
FIGS. 5A and 5B show data of three dimensions obtained from use of the apparatus of FIG. 1 with a selected subject in a two dimensional plot, FIGS. 6A(i)–(iii) and 6B(i)–(iii) show graphs of corresponding references for, and corresponding averages of selected data obtained from, the data used in the plots of FIGS. 2A and 2B through 5A and 5B, FIGS. 7A, 7B and 7C show comparative plots of values of indices found for selected subjects obtained from the use of the apparatus of FIG. 1 with such subjects.
Figure 5B:
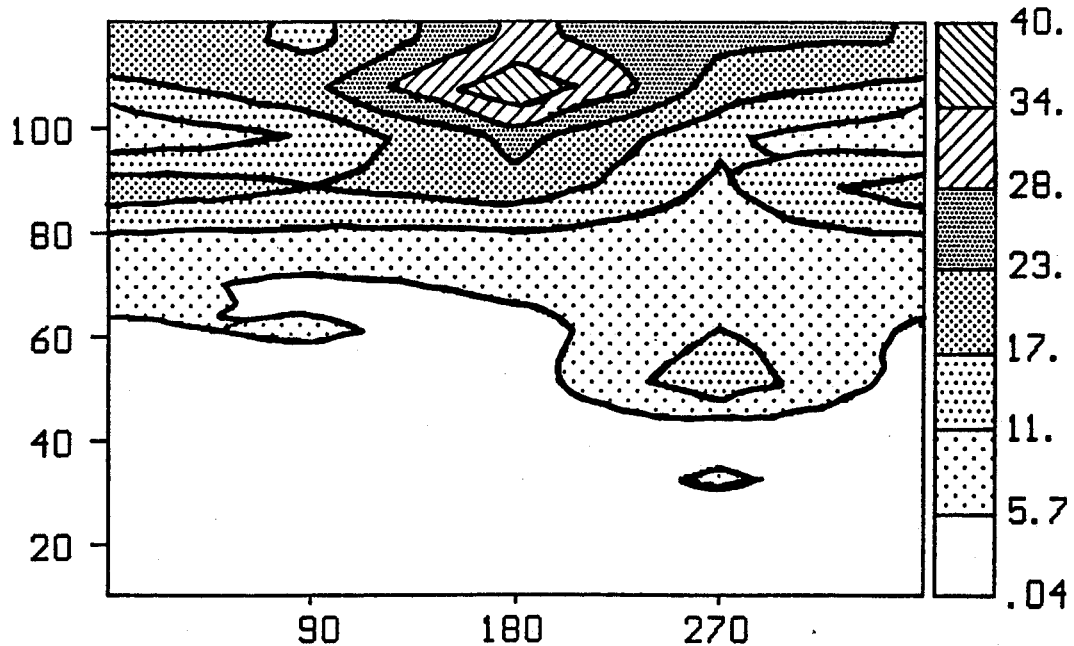

FIGS. 5A and 5B show the results for a subject who has defects in the stretch reflex of both the flexor and the extensor muscles being measured in connection with testing that subject's wrist joint response in following the target sinusoidal position path. As can be seen in FIG. 5A, the electromyographic signal strength is concentrated to a substantial degree at the 0°/360° phase point clearly showing that the stretch reflex of the flexor muscle is being activated at such times as to brake the activity of the extensor muscle in reaching the next full extension position for the hand. Here, though, there is some aid being provided the flexor muscle to reach the next full flexion position of the hand. But this effort is being braked by the extensor muscle as shown in FIG. 5B where the electromyographic signal data is clearly concentrated about the 180° phase point. Relatively little electromyographic signal strength occurs at the 0°/360° phase point to suggest that the stretch reflex of this extensor muscle is aiding the volitional directives urging the hand reach the next full extension position.

If plots of the kind shown in FIGS. 2 through 5 are averaged along the time axis on the ordinates therein, graphs of the kind shown in some of FIGS. 6A(i–iii) and 6B(i–iii) result. FIGS. 6A(i) and 6B(i) show just for reference the repeated sinusoidal path cycle followed by the target which is to be tracked by the subject under test. The dashed line pairs along the phase axis, or abscissa, represent the required successful tracking ranges about potential impulsive torque deliverance phase points in which potential impulsive torque deliverances can occur. The 90° point and the 270° points again represent the maximum extension position of the hand with respect to the forearm and the maximum flexion position of the hand with respect to the forearm, respectively.

FIG. 6A(ii) shows a graph which is the result of such a time averaging of the previous kinds of plots in FIGS. 2A and 2B through 5A and 5B. The solid line shows a typical graph found for a normal person. The dashed line graph shows results for persons suffering from Parkinson's disease, and clearly shows that the reflex electromyographic signal strength is shifted leftward to different phase points and so to a different time with respect to that of a normal person.

FIG. 6A(iii) shows the result obtained from the volitional matrix resulting from the tests. As can be seen, for a normal person, the stretch reflex electromyographic signal strength comes just ahead of the phase points where the volitional electromyographic signal strength is concentrated and so aids the volitional movement. For a sufferer of Parkinson's disease, however, the stretch reflex electromyographic signal strength is concentrated well before the concentration of the volitional electromyographic signal strength and, as can be seen in FIG. 6B(ii), is reaching peaks just when the reflex signal strength for the opposite extensor muscle should be at a peak thus causing braking of the movement to be forced by that extensor muscle.

The situation with respect to the extensor muscle shown in FIG. 6B(ii) for the stretch reflex thereof and FIG. 6B(iii) for the volitional directives to that muscle gives a similar result. Again, the solid line in the stretch reflex graph of FIG. 6B(ii) is for a normal person with the dashed line being that for a sufferer from Parkinson's disease. Once again, the stretch reflex signal strength occurs at a different phase point and so at a different time for one suffering from Parkinson's disease than it does for a normal person. Again, this leads to a time displacement with respect to the volitional signal strength concentration and results in braking activity occurring in the extensor muscle if there has been proper movement activity initiated by the flexor muscle.

This situation of normal persons' outcomes from this testing versus outcomes of sufferers from Parkinson's disease for essentially the same testing can be made quantitative by forming suitable indices representing the conditions just described. These indices can be based on the electromyographic signal strength occurring in the 40 to 120 ms portion of the 0 to 120 ms data collection range in which data is collected after the target has been suitably closely tracked through the potential impulsive torque deliverance points in the target position sinusoidal path. Time averages over this time duration have been found sufficient to cover essentially all of the significant electromyographic signal amplitudes occurring in the modulation of the stretch reflex and in the volitional directives.

The indices are based, however, on only the 0°/360° potential impulsive torque deliverance point and the 180° potential impulsive torque deliverance point. Time averages from these two phase points were chosen because they represent the maximum velocity of the tracking movement in approaching the next full extension position of the hand and in approaching the next full flexion position of the hand, respectively. These are the points when one or the other of the extensor muscle and the flexor muscle should be making their maximum contracting effort while the other should be making little contracting effort but, rather, lengthening.

Thus, at the 0°/360° phase point, the extensor muscle would be providing maximum assistance in its stretch reflex to the volitional directives while the flexor muscle should be lengthening so that any contracting effort by this latter muscle represents a braking of the motion being caused by the extensor muscle. Similarly, at the 180° phase point, the flexor muscle should be providing its greatest assistance to the volitional directive of forcing the hand to its next full extension, and the extensor muscle should be lengthening so that any electromyographic signals indication contraction thereof will act to brake the motion being caused by the flexor muscle.

A first suitable index is the reflex log assistive/braking ratio which is the logarithm to the base ten of the ratio of (a) the average stretch reflex electromyographic signal strength in the 40 to 120 ms duration data collections described above at the cyclic maximum contracting effort phase point for the muscle involved (or the maximum hand velocity point), to (b) the average stretch reflex electromyographic signal strength for the same time range taken at that tracking phase point in which the hand is at maximum velocity during the cyclic lengthening of that same muscle due to the contracting of the opposite muscle in an agonist-antagonist pair.

For the extensor muscle involved, this index would be the base ten logarithm of the ratio of (a) the average electromyographic signal strength occurring at the 0°/360° phase point over 40 to 120 ms in the reflex matrix for that muscle, to (b) the average electromyographic signal strength occurring at the 180° phase point in that matrix (this data could be taken from any of the figure "B" plots found in any of FIGS. 2B through 6B). In this ratio, the numerator value could be either of the values marked "N" in FIG. 6B(ii) (depending on which of the two tested subjects represented by the two curves shown, one normal and one suffering from Parkinson's disease, was of interest), and the denominator value could be either of the values marked "D" in that figure.

For the corresponding flexor muscle, the reverse will be true so that the index will be the base ten logarithm of the ratio of (a) the time average for 40 to 120 ms of the electromyographic ( signal data occurring at the 180° phase point in the reflex matrix for that muscle, to (b) the time average over that same time range of the electromyographic signal data occurring at the 0°/360° phase point in that matrix (this data could be taken from any of the "A" plots of FIGS. 2A through 5A). In this ratio, the numerator value could be either of the values marked "N" in FIG. 6A(ii) (again depending on which subject was of interest), and the denominator value could be either of the values marked "D" in that figure.

An analogous volitional electromyographic signal index is the volitional log assistive/braking ratio which is the base 10 logarithm of the ratio of (a) the time average over the same 40–120 ms time duration of the electromyographic signal strength for volitional only electromyographic signals at the point of maximum velocity of the hand being forced by the muscle involved during its contraction, to (b) the time averaged volition only electromyographic signal strength at the phase point where the hand is at maximum velocity due to the contraction of the opposite muscle leading to the lengthening of the muscle involved. As indicated above, volition only electromyographic signal data is that data obtained in the testing described above forming the pertinent volition matrix. The same procedure is followed in forming this index involving volition for the extensor and flexor muscles involved as was followed above using the reflex matrix for these muscles.

Although no plots have been presented of the type shown in FIGS. 2A and 2B through 5A and 5B for volition only electromyographic data, similar plots can be constructed from such data as is found in the corresponding volition matrix and so the information for this volition index could be found from such plots. This ratio of this volition index could, for the subject represented, be formed from the data values found in FIGS. 6A(iii) and 6B(iii) for the flexor and extensor muscles measured, respectively, using the values marked "N" for numerators and values marked "D" for denominators.

Figure 7A:
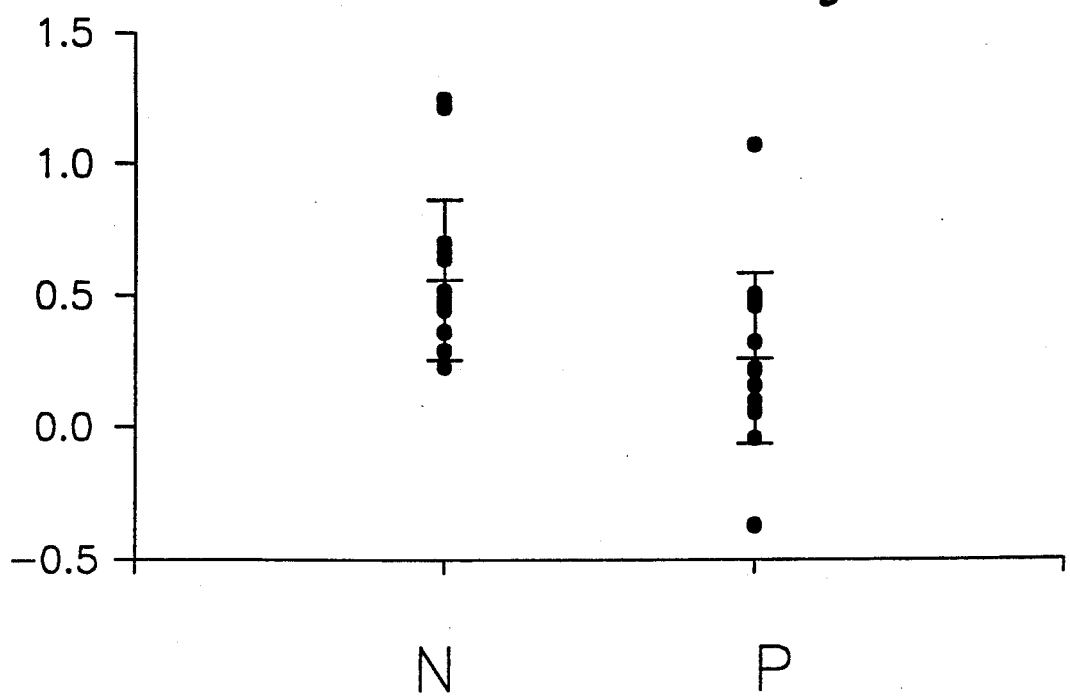
Figure 7B:
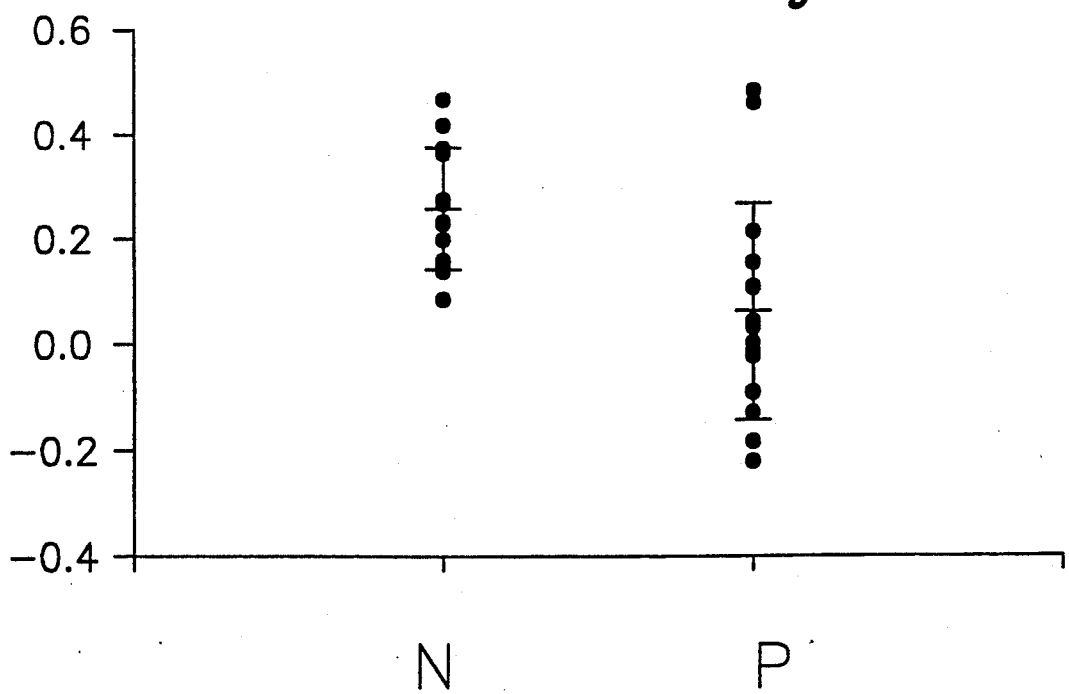
Figure 7C:
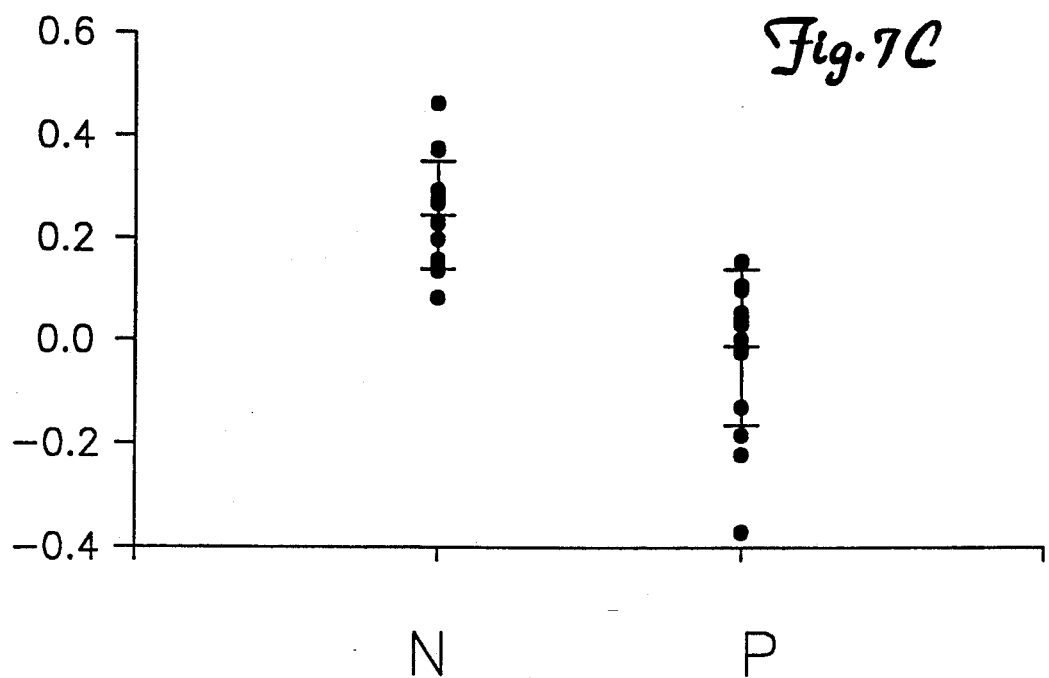

The higher the value of one of these log ratios the greater the increase in the stretch reflex assisting the volitional directives or the greater the decrease in braking the motion caused by the opposite muscle involved in operating the joint. (The logarithm of the ratio found is used to linearize the scale.) Graphs of such reflex log assistive/braking ratios determined for a group of normal persons and a group of sufferers of Parkinson's disease are shown in FIGS. 7A and 7B for the flexor and extensor muscles thereof under test in those subjects, respectively. As can be seen, the ratios cluster about lower values for sufferers of Parkinson's disease in the column labeled "P" than they do for normal persons in the column labeled "N". A worst case selection of the worst of the ratios for each of subject under test gives the results shown in FIG. 7C. Clearly, selecting the worst of these ratios for each of the people involved increases the tendency of the ratios to differ in clustering about values for normal persons versus those suffering from Parkinson's disease.

Figure 8A:
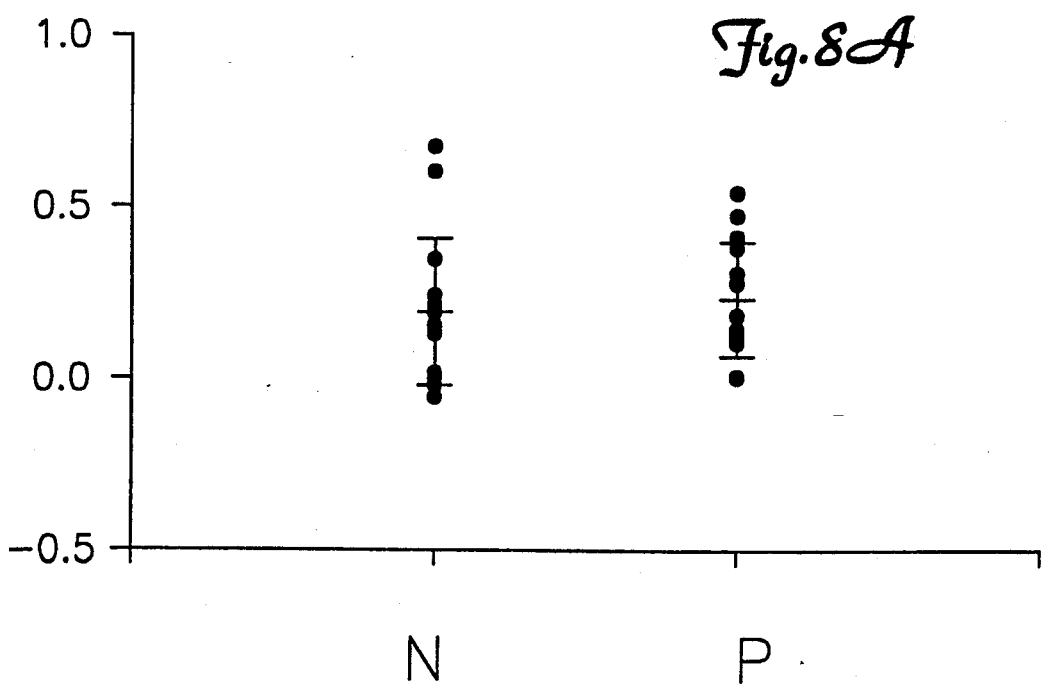

Similar graphs of volitional log assistive/braking ratios determined for these same subjects are shown in FIGS. 8A, 8B and 8C for ratios based on volition only electromyographic data. Little difference occurs, if any, between normal persons and those suffering from Parkinson's disease thus confirming that, for Parkinson's disease suffers, stretch reflex defects are involved to a more significant degree for these test subjects than are any volitional defects. The test subjects which are sufferers of Parkinson's disease in all of these plots are confirmed to be so suffering through several other kinds of clinical tests.

Two further indices can be found for each of the muscles involved which tend to isolate the assistive aspects and the braking aspects of the electromyographic signals. The log assistive/mean ratio is the base 10 logarithm ratio of (a) the time average over the same time of the stretch reflex electromyographic signal strength taken at the phase point at which the hand has maximum velocity due to the contraction of the muscle involved, to (b) the time average of the electromyographic signal strength at both the phase point at which the hand achieves maximum velocity due to the contraction of the muscle involved and at the phase point at which the hand, due to the contracting of the opposite muscle operating the joint, achieves maximum velocity leading to the muscle involved lengthening, and at the maximum flexion and extension phase points. The log braking/mean ratio is the base 10 logarithm, of the ratio of (a) the time averaged electromyographic signal data taken at the phase point where the hand has the maximum velocity, due to the contraction of the opposite muscle operating the joint, leading to the muscle involved lengthening, to (b) the time average of electromyographic signal strength at both the phase point at which the hand achieves maximum velocity due to the contraction of the muscle involved and at the phase point at which the hand, due to the opposite muscle operating the joint, achieves maximum velocity, and at the maximum flexion and extension points.

Finally, there is the joint actions of the agonist and antagonist muscles, or the flexor and extensor muscles being measured in connection with the wrist test described above, which must be considered insofar as their being co-activated. Two further indices for giving an indication of this are based on the reflex matrix described above and the volition matrix described above for each of these muscles. These indices were constructed by first normalizing the elements of each matrix for each muscle by the mean of that matrix and then replacing resulting elements which fall below a threshold value such as 0.25 by zero. Corresponding elements from the reflex matrices were compared with the smaller element in each such correspondence being divided by the larger element to form a new matrix with any division by zero situations arising leading to a zero inserted in the new matrix. The elements of the new matrix associated with stretch reflex data were then summed to yield a single value, the reflex electromyographic co-activation indicator, which increases with increases in joint reflex electromyographic signal strengths occurring in the flexor and extensor muscles.

Similar steps were taken with the normalized and substituted volitional matrices for these two muscles to define the volitional electromyographic signal co-activation indicator.

Figure 9:
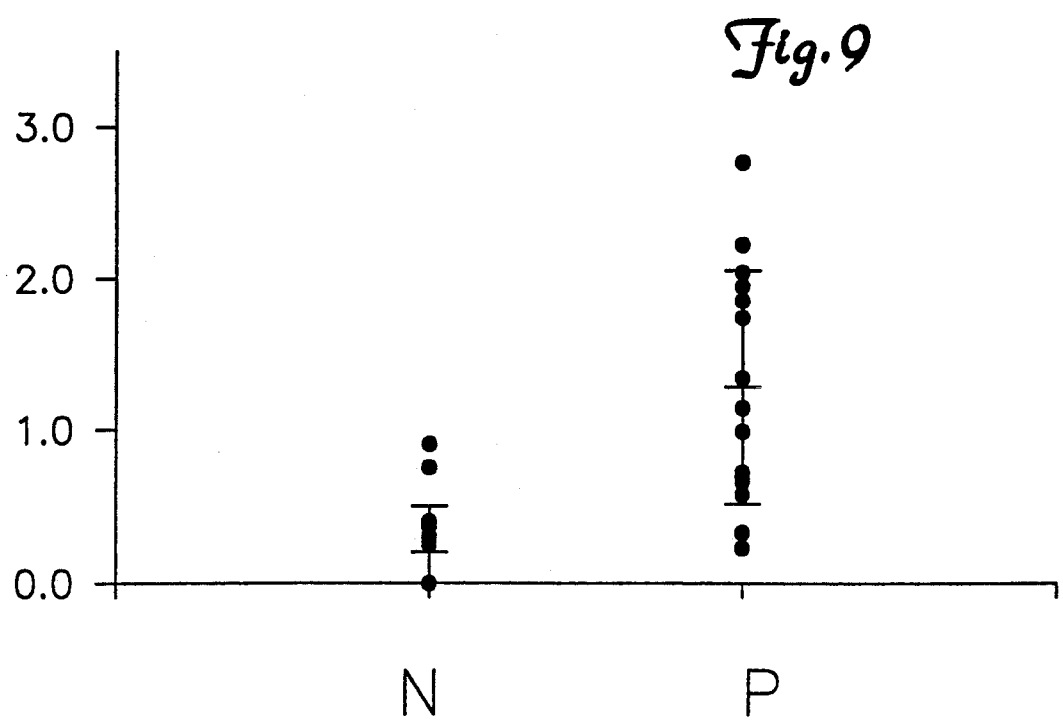
FIG. 9 shows comparative plots of values of an index found for selected subjects obtained from the use of the apparatus of Figure with such subjects.
Figure 10:
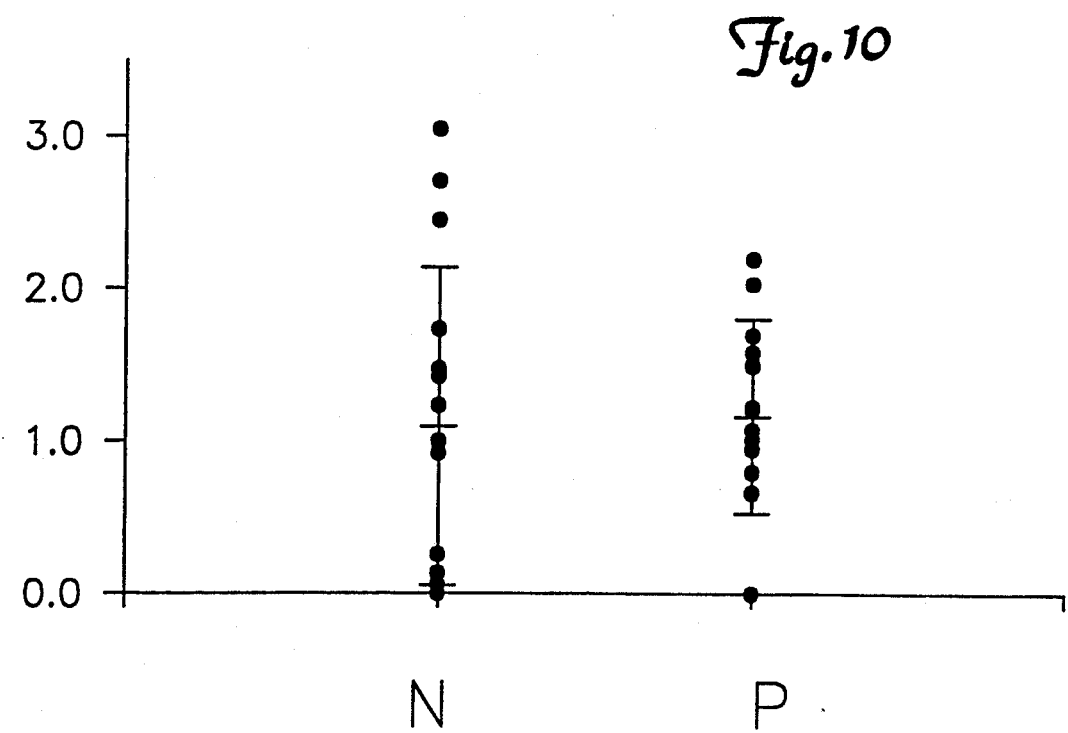
FIG. 10 shows comparative plots of values of an index found for selected subjects obtained from the use of the apparatus of FIG. 1 with such subjects.

These indices are shown for again the same group of normal subjects and a group of sufferers from Parkinson's disease in FIGS. 9 and 10. FIG. 9, representing a joint indicator based on the stretch reflex data matrices, shows a relatively low value grouping for normal persons, but a much higher value for sufferers from Parkinson's disease although there is some overlap. FIG. 10, on the other hand, based on volitional data matrices, shows there is no significant difference in groupings between normal persons and those suffering from Parkinson's disease. Thus, again, these data show that stretch reflex deficiencies are much more closely associated with sufferers of Parkinson's disease than are any volitional directive deficiencies.

Although the present invention has been described with reference to preferred embodiments, workers skilled in the art will recognize that changes may be made in form and detail without departing from the spirit and scope of the invention.

What is claimed is:

1. A method for treating selected myographic signals obtained from a first muscle for operating a skeletal joint in a body subject to both volitional motion and externally forced motion to provide a first index based thereon indicative of control directives provided to said first muscle during contractions and lengthenings thereof, said method comprising:

directing volitionally said first muscle to cause an actuator portion of said joint to follow a moving target with respect to a base portion of said joint while a bodily portion extending from said actuator portion of said joint is connected to a mechanical means, said mechanical means for selectively providing applications of external controlled forces to said bodily portion;

acquiring a first plurality of representations of electromyographic signal portions from said first muscle with each such electromyographic signal portion therein occurring during a corresponding volitional contraction of said first muscle as part of a plurality of volitional contractions thereof with selected ones of said plurality of volitional contractions being accompanied by a corresponding application of a selected external controlled force applied for a selected duration to said first muscle by said mechanical means;

acquiring a second plurality of representations of electromyographic signal portions from said first muscle with each such electromyographic signal portion therein occurring during a corresponding lengthening of said first muscle as part of a plurality of lengthenings thereof with selected ones of said plurality of lengthenings being accompanied by a corresponding application of a selected external controlled force applied for a selected duration to said first muscle by said mechanical means; and forming said first index based on values of those of said first plurality of representations of electromyographic signal portions which have occurred in conjunction with an occurrence of a said application of an external controlled force relative to values of those of said second plurality of representations of electromyographic signal portions which have occurred in conjunction with an occurrence of said application of an external controlled force.

2. The method of claim 1 further comprising forming a second index based on values of those of said first plurality of representations of electromyographic signal portions which have occurred absent any coincidental occurrence of a said application of an external controlled force relative to values of those of said second plurality of representations of electromyographic signal portions which have occurred absent any coincidental occurrence of a said application of an external controlled force.

3. The method of claim 2 wherein said second index is based on a ration of values of those of said first plurality of representations of electromyographic signal portions which have occurred absent any coincidental occurrence of a said application of an external controlled force to values of those of said second plurality of representations of electromyographic signal portions which have occurred absent any coincidental of a said application of an external controlled force.

4. The method of claim 3 wherein said second index is based on said ratio by being dependent on a logarithm of said ratio.

5. The method of claim 4 wherein each said electromyographic signal portion in said first plurality of representations of electromyographic signal portions which has occurred in conjunction with an occurrence of a said application of an external controlled force has subtracted therefrom a value based on an average of values of those of said first plurality of representations of electromyographic signal portions which have occurred absent any coincidental occurrence of a said application of an external controlled force.

6. The method of claim 1 further comprising forming a second index based on values of those of said first plurality of representations of electromyographic signal portions which have occurred in conjunction with an occurrence of a said application of an external controlled force relative to values of those of both of said first and second pluralities of representations of electromyographic signal portions which have occurred in conjunction with an occurrence of a said application of an external controlled force.

7. The method of claim 6 wherein each said electromyographic signal portion in said first plurality of representations of electromyographic signal portions which has occurred in conjunction with an occurrence of a said application of an external controlled force has subtracted therefrom a value based on an average of values of those of said first plurality of representations of electromyographic signal portions which have occurred absent any coincidental occurrence of a said application of an external controlled force.

8. The method of claim 6 wherein said second index is based on a ratio of values of said first plurality of representations of electromyographic signal portions which have occurred in conjunction with an occurrence of a said application of an external controlled force to values of those of both of said first and second pluralities of representations of electromyographic signal portions which have occurred in conjunction with an occurrence of a said application of an external controlled force.

9. The method of claim 8 wherein said second index is based on said ratio by being dependent on a logarithm of said ratio.

10. The method of claim 9 wherein each said electromyographic signal portion in said first plurality of representations of electromyographic signal portions which has occurred in conjunction with an occurrence of a said application of an external controlled force has subtracted therefrom a value based on an average of values of those of said first plurality of representations of electromyographic signal portions which have occurred absent any coincidental occurrence of a said application of an external controlled force.

11. The method of claim 1 further comprising forming a second index based on values of those of said second plurality of representations of electromyographic signal portions which have occurred in conjunction with an occurrence of a said application of an external controlled force relative to values of those of both of said first and second pluralities of representations of electromyographic signal portions which have occurred in conjunction with an occurrence of a said application of an external controlled force.

12. The method of claim 11 wherein each said electromyographic signal portion in said first plurality of representations of electromyographic signal portions which has occurred in conjunction with an occurrence of a said application of an external controlled force has subtracted therefrom a value based on an average of values of those of said first plurality of representations of electromyographic signal portions which have occurred absent any coincidental occurrence of a said application of an external controlled force.

13. The method of claim 11 wherein said second index is based on a ratio of values of those of said second plurality of representations of electromyographic signal portions which have occurred in conjunction with an occurrence of a said application of an external controlled force to values of those of both of said first and second pluralities of representations of electromyographic signal portions which have occurred in conjunction with the occurrence of a said application of an external controlled force.

14. The method of claim 13 wherein said second index is based on said ratio by being dependent on a logarithm of said ratio.

15. The method of claim 14 wherein each said electromyographic signal portion in said first plurality of representations of electromyographic signal portions which has occurred in conjunction with an occurrence of a said application of an external controlled force has subtracted therefrom a value based on an average of values of those of said first plurality of representations of electromyographic signal portions which have occurred absent any coincidental occurrence of a said application of an external controlled force.

16. The method of claim 1 wherein each said electromyographic signal portion in said first plurality of representations of electromyographic signal portions which has occurred in conjunction with an occurrence of a said application of an external controlled force has subtracted therefrom a value based on an average of values of those of said first plurality of representations of electromyographic signal portions which have occurred absent any coincidental occurrence of a said application of an external controlled force.

17. The method of claim 1 wherein each said electromyographic signal portion in said first plurality of representations of electromyographic signal portions which has occurred in conjunction with an occurrence of a said application of an external controlled force is divided by a value based on an average of values of those of said first plurality of representations of electromyographic signal portions which have occurred absent any coincidental occurrence of a said application of an external controlled force.

18. The method of claim 1 further comprising:
acquiring a third plurality of representations of electromyographic signal portions from a second muscle in said body with each such electromyographic signal portion occurring during a corresponding volitional contraction of said second muscle as part of a plurality of volitional contractions with selected ones of said plurality of volitional contractions being accompanied by a corresponding application of a selected external controlled force applied for a selected duration to said second muscle by said mechanical means; and acquiring a fourth plurality of representations of electromyographic signal portions from said second muscle with each such electromyographic signal portion occurring during a corresponding lengthening of said second muscle as part of a plurality of lengthenings thereof with selected ones of said plurality of lengthenings being accompanied by a corresponding application of a selected external controlled force applied for a selected duration to said second muscle by said mechanical means.

19. The method of claim 18 further comprising forming a second index based on values of those of said third plurality of representations of electromyographic signal portions which have occurred in conjunction with an occurrence of a said application of an external controlled force relative to values of those of said fourth plurality of representations of electromyographic signal portions which ave occurred in conjunction with an occurrence of a said application of an external controlled force.

20. The method of claim 19 wherein each of said plurality of volitional contractions of said first muscle has a corresponding one of said plurality of lengthenings of said second muscle, and each of said plurality of lengthenings of said first muscle has a corresponding one of said plurality of volitional contractions of said second muscle.

21. The method of claim 20 wherein said first muscle and said second muscle are alternatingly agonist and antagonist muscles for operating a skeletal joint and are volitionally directed to cause an actuator portion of said joint to follow a reciprocating position target with respect to said base of said joint while said actuator side of said joint is in a bodily portion connected to said mechanical means.

22. The method of claim 20 wherein there is a correspondence between each said representation in said first plurality of representations of electromyographic signal portions and a said representation in said third plurality of representations of electromyographic signal portions due to similarities in conditions in acquiring each of said corresponding representations, and wherein said method further comprises forming a joint plurality of representations with each such representation in said joint plurality being based on relative values of a corresponding pair of correspondence representations from said first and third pluralities of representations of electromyographic signal portions, and forming a joint index based on values of said joint plurality of representation.

23. The method of claim 20 wherein there is a correspondence between each said representation in said second plurality of representations of electromyographic signal portions and a said representation in said fourth plurality of representations of electromyographic signal portions due to similarities in conditions in acquiring each of said corresponding representations, and wherein said method further comprises forming a joint plurality of representations with each such representation in said joint plurality being based on relative values of a corresponding pair of correspondence representations from said second and fourth pluralities of representations of electromyographic signal portions, and forming a joint index based on values of said joint plurality of representation.

24. The method of claim 1 wherein said first index is based on a ratio of values of those of said first plurality of representations of electromyographic signal portions which have occurred in conjunction with an occurrence of a said application of an external controlled force to values of those of said second plurality of representations of electromyographic signal portions which have occurred in conjunction with an occurrence of a said application of an external controlled force.

25. The method of claim 24 wherein said first index is based on said ratio by being dependent on a logarithm of said ratio.

26. The method of claim 25 wherein each aid electromyographic signal portion in said first plurality of representations of electromyographic signal portions which as occurred in conjunction with an occurrence of a said application of an external controlled force has subtracted therefrom a value based on an average of values of those of said first plurality of representations of electromyographic signal portions which have occurred absent any coincidental occurrence of a said application of an external controlled force.

* * * * *

UNITED STATES PATENT AND TRADEMARK OFFICE
CERTIFICATE OF CORRECTION

PATENT NO. : 5,263,489

DATED : November 23, 1993

INVENTOR(S) : MICHAEL T.V. JOHNSON, ALEXANDER KIPNIS

It is certified that error appears in the above-identified patent and that said Letters Patent is hereby corrected as shown below:

Col. 6, line 56, after "handle", insert --position,--

Col. 6, line 56, after "position of", insert --a--

Col. 12, line 7, after "electromyographic", delete --(--

Col. 15, line 5, delete "ration", insert --ratio--

Col. 17, line 25, delete "ave", insert --have--

Signed and Sealed this

Seventeenth Day of May, 1994

BRUCE LEHMAN

*Attest:*

*Attesting Officer*  *Commissioner of Patents and Trademarks*